United States Patent [19]

Gray et al.

[11] Patent Number: 5,846,813
[45] Date of Patent: Dec. 8, 1998

[54] DSZD UTILIZATION IN DESULFURIZATION OF DBT BY RHODOCOCCUS SP. IGTS8

[75] Inventors: Kevin A. Gray; Charles H. Squires; Daniel J. Monticello, all of The Woodlands, Tex.

[73] Assignee: Energy BioSystems Corporation, The Woodlands, Tex.

[21] Appl. No.: 583,118

[22] PCT Filed: Dec. 5, 1995

[86] PCT No.: PCT/US95/15864

§ 371 Date: Feb. 27, 1996

§ 102(e) Date: Feb. 27, 1996

Related U.S. Application Data

[60] Provisional application No. 60/004,105 Sep. 21, 1995.

[51] Int. Cl.$^6$ .............................. C12N 9/02; C12N 1/20; C10G 32/00; C07H 21/04
[52] U.S. Cl. ......................... 435/282; 435/281; 435/189; 435/252.3; 435/320.1; 536/23.2; 935/22
[58] Field of Search ................................ 435/282, 252.3, 435/325, 320.1; 536/23.2; 935/22

[56] References Cited

U.S. PATENT DOCUMENTS

| | | | |
|---|---|---|---|
| 5,002,888 | 3/1991 | Kilbane, II | 435/252.31 |
| 5,104,801 | 4/1992 | Kilbane, II | 435/282 |
| 5,132,219 | 7/1992 | Kilbane, II | 435/195 |
| 5,198,341 | 3/1993 | Kilbane, II | 435/42 |
| 5,344,778 | 9/1994 | Kilbane, II | 435/262 |
| 5,356,801 | 10/1994 | Rambosek et al. | 435/195 |
| 5,356,813 | 10/1994 | Monticello | 435/282 |
| 5,358,870 | 10/1994 | Monticello et al. | 435/282 |

FOREIGN PATENT DOCUMENTS

| | | |
|---|---|---|
| 94/01563 | 1/1994 | WIPO . |

OTHER PUBLICATIONS

Ohshiro, takashi et al., "Enzymatic desulfurization of dibenzothiophene by a cell–free system of *Rhodococcus erythropolis* D–1," *FEMS Microbiology Letters*, 118:341–344 (1994).

Ohshiro, Takashi et al., "Involvement of Flavin Coenzyme in Dibenzothiophene Degrading Enzyme System from *Rhodococcus erythropolis* D–1," *Biosci. Biotech. Biochem.*, 59(7): 1349–1351 (1995).

Piddington, Christopher S. et al., "Sequence and Molecular Characterization of a DNA Region Encoding the Dibenzothiophene Desulfurization Operon of *Rhodococcus* sp. Strain IGTS8," *Applied and Environmental Microbiology*, 61(2) :468–475 (1995).

Nagy, István et al., "Characterization of the *Rhodococcus sp.* NI86/21 gene encoding alcohol: N,N'–dimethyl–4–nitrosoaniline oxidoreductase inducible by atrazine and thiocarbamate herbicides," *Arch Microbiol.*, 163:439–446 (1995.

Monticello, Daniel J. and Kilbane, John J., "Practical Considerations in Biodesulfurization of Petroleum," *IGT's Third International Symposium on Gas Oil, Coal and Environmental Biotechnology*, Dec. 3–5, 1990, New Orleans, Louisiana.

*Primary Examiner*—Rebecca E. Prouty
*Assistant Examiner*—Einar Stole
*Attorney, Agent, or Firm*—Hamilton, Brook, Smith & Reynolds, P.C.

[57] ABSTRACT

The invention relates to the discovery that the rate of reaction of the desulfurization of fossil fuels is enhanced by the addition of an oxidoreductase to the biocatalyst. The invention is drawn to a method for enhancing the rate of desulfurizing a fossil fuel containing organic sulfur compounds, comprising the steps of:

a) contacting the fossil fuel with an aqueous phase containing a biocatalyst capable of cleaving carbon-sulfur bonds and a rate-enhancing amount of an oxidoreductase, thereby forming a fossil fuel and aqueous phase mixture;

b) maintaining the mixture of step (a) under conditions sufficient for cleavage of the carbon-sulfur bonds of the organic sulfur molecules by the biocatalyst, thereby resulting in a fossil fuel having a reduced organic sulfur content; and c) separating the fossil fuel having a reduced organic sulfur content from the resulting aqueous phase. The invention also relates to a recombinant microorganism containing one or more recombinant DNA molecules which encode a biocatalyst capable of desulfurizing a fossil fuel containing organic sulfur molecules and which encode an oxidoreductase. The invention also relates to a composition comprising (a) a biocatalyst capable of desulfurizing a fossil fuel containing organic sulfur molecules and (b) an oxidoreductase.

20 Claims, 6 Drawing Sheets

```
GGTACCTCGACTGTCGTCATCGCGAAGCTAGTCCTCTCGTGAAGCTGGGTAAAGCGCAGGTCAGTGAAGTGC     72
AACATCTAGAACGTGTTCTAGTTCAATGTTAGCAGTGATGAAAAGCTACTGGGGATCGTAGTCGCCGAGCAA    144
CACGTTCCCGATCAGCGGGAACCACGGCAGTCTGATCCGGCCTTCCTGGCGGTCCGGGGTGGCGACGACCTG    216
CCCGAACGGGCGGTTCGCCGGCGGCGTCCGGGCGGTTGAGCTGCCGAAGTCTGTGCACGGGGTGTTTGTCGG    288
TACACAGTGGGAACCAGGTGAGACGCCGGTCACAAAGAATCGGCTCGAATCCCTCCCGCAGTCATATTCGTG    360
CACATCCATGAGGAGATACCGATGGCTATCGAGCTCAACCAGATCTGGGACTTTCCGATCAAGGAGTTCCAC    432
                  M   A   I   E   L   N   Q   I   W   D   F   P   I   K   E   F   H
CCCTTCCCGCGCGCCCTGATGGGTGTGGGCGCTCACGACATCATCGGTGTGGAGGCCAAGAATCTCGGCTTC    504
   P   F   P   R   A   L   M   G   V   G   A   H   D   I   I   G   V   E   A   K   N   L   G   F
AAGCGCACCCTTCTGATGACGACCGGTCTGCGCGGTTCGGGCATCATCGAGGAACTCGTCGGCAAGATCGAG    576
   K   R   T   L   L   M   T   T   G   L   R   G   S   G   I   I   E   E   L   V   G   K   I   E
TACCAGGGTGTCGAGGTCGTGCTCTACGACAAGGTCGAGTCGAATCCCAAGGACTACAACGTCATGGAGGCC    648
   Y   Q   G   V   E   V   V   L   Y   D   K   V   E   S   N   P   K   D   Y   N   V   M   E   A
GCGGCTCTCTATCAGAAGGAGAAGTGCGACTCGATCATCTCGATCGGCGGTGGTTCGAGCCACGACGCCGCC    720
   A   A   L   Y   Q   K   E   K   C   D   S   I   I   S   I   G   G   G   S   S   H   D   A   A
AAGGGTGCTCGCGTCGTGATCGCACACGACGGTCGCAACATCAACGAGTTCGAGGGCTTCGCCAAGTCCACC    792
   K   G   A   R   V   V   I   A   H   D   G   R   N   I   N   E   F   E   G   F   A   K   S   T
AACAAGGAGAACCCGCCGCATATCGCCGTATCCACTACGGCTGGAACGGGTTCCGAGACGTCGTGGGCATAC    864
   N   K   E   N   P   P   H   I   A   V   S   T   T   A   G   T   G   S   E   T   S   W   A   Y
GTCATCACTGACACCTCGGACATGAACAACCCGCACAAGTGGGTGGGCTTCGACGAGGCGACCATCGTCACG    936
   V   I   T   D   T   S   D   M   N   N   P   H   K   W   V   G   F   D   E   A   T   I   V   T
TTGGCGATCGACGATCCGCTGCTCTACTACACCTGCCCTCAGCATTTCACCGCGTACTGCGGCTTCGACGTA   1008
   L   A   I   D   D   P   L   L   Y   Y   T   C   P   Q   H   F   T   A   Y   C   G   F   D   V
CTCGCGCACGGCAGTGAGCCTTTCGTTTCTCGTCTCGATTTCGCGCCTTCGCTCGGTAACGCGATCTACTCG   1080
   L   A   H   G   S   E   P   F   V   S   R   L   D   F   A   P   S   L   G   N   A   I   Y   S
GTCGAGTTGGTCGCGAAGAACCTGCGCGAGGCCGTCTTCGAGCCGCGTAACCTCAAGGCGCGCGAGGGAATG   1152
   V   E   L   V   A   K   N   L   R   E   A   V   F   E   P   R   N   L   K   A   R   E   G   M
ATGAACGCGCAGTACATTGCCGGACAGGCCTTCAACTCCGGTGGCCTCGGCATCGTTCACTCGATCTCGCAC   1224
   M   N   A   Q   Y   I   A   G   Q   A   F   N   S   G   G   L   G   I   V   H   S   I   S   H
GCGGTCAGTGCATTCTTCGACAGCCACCACGGTTTGAACAACGCCATCGCGTTGCCGCGTGTGTGGGAGTAC   1296
   A   V   S   A   F   F   D   S   H   H   G   L   N   N   A   I   A   L   P   R   V   W   E   Y
AACCTGCCTTCGCGTTACGAGCGCTACGCCCAGTTGGCCGGCGCACTCGGTGTCGACACTCGCAACCTCACC   1368
   N   L   P   S   R   Y   E   R   Y   A   Q   L   A   G   A   L   G   V   D   T   R   N   L   T
ACGGTTCAGGCCGCGGATGCTGCCGTCGAGGCTGCCATTCGTCTGGCCAAGGACGTCGGTATCCCCGACAAC   1440
   T   V   Q   A   A   D   A   A   V   E   A   A   I   R   L   A   K   D   V   G   I   P   D   N
TTCGGGCAGGTTCGCACAGACTCGTACGCGAAGAACCAGATGAACACCAAGAAGTACGAGGGTCGTGGTGAT   1512
   F   G   Q   V   R   T   D   S   Y   A   K   N   Q   M   N   T   K   K   Y   E   G   R   G   D
GTCATCAAGGGTGACGAGAAGACTGTGCGCGCCATCTCCGAGCACATTCAGGACGACTGGTGCACCCCGGGT   1584
   V   I   K   G   D   E   K   T   V   R   A   I   S   E   H   I   Q   D   D   W   C   T   P   G
AACCCCCGTGAGGTCACTGTGGAGTCGATGATCCCGGTTGTCGATCACGCGATCAACAAGTCGTACTTCTAG   1656
   N   P   R   E   V   T   V   E   S   M   I   P   V   V   D   H   A   I   N   K   S   Y   F
CAGGGCCTCCGGCCCCGTGCGCGCTTAAGGAGTCCAGAGACTCCTCGAGCGCGCACAGGGGCTGTGCCCCTA   1728
TCGAAAGGTATTCCATGTCCGGTCGCAGTTTCTCCAGCGGAATCGAAGTGAAAGATGCTCTGCGAGAGCAGG   1800
                        M   S   G   R   S   F   S   S   G   I   E   V   K   D   A   L   R   E   Q
ACTACATTGCCGATGACGAGTTCGCGGTAGTCGTTCATCTGGCGACGGCGCTGGGGCGTCCGCTCCTGCTCG   1872
   D   Y   I   A   D   D   E   F   A   V   V   V   H   L   A   T   A   L   G   R   P   L   L   L
AAGGGCCGGCCGGTGTCGGTAAGACGGAACTGGCGAAGTCTCTGGCTGCGATCGGGGGCCGCAAACTGGTGC   1944
   E   G   P   A   G   V   G   K   T   E   L   A   K   S   L   A   A   I   G   G   R   K   L   V
GATTGCAGTGTTACGAAGGGCTGGACGACAATCGAGCCCTGTACGAATGGGACTACGCGAACGAACTCCTGC   2016
   R   L   Q   C   Y   E   G   L   D   D   N   R   A   L   Y   E   W   D   Y   A   N   E   L   L
ACGTGCAGATGCTTCGCGACCGGATCAGTGATCAGGTTTCCGAATTC                            2063
   H   V   Q   M   L   R   D   R   I   S   D   Q   V   S   E   F
```

Figure 6

DSZD UTILIZATION IN DESULFURIZATION OF DBT BY RHODOCOCCUS SP. IGTS8

This application is the national stage of PCT/US95/15864, filed Dec. 5, 1995, which claims priority to U.S. provisional application 60/004,105, filed Sep. 21, 1995.

BACKGROUND OF THE INVENTION

The microbial desulfurization of fossil fuels has been an area of active investigation for over fifty years. The object of these investigations has been to develop biotechnology based methods for the pre-combustion removal of sulfur from fossil fuels, such as coal, crude oil and petroleum distillates. The driving forces for the development of desulfurization methods are the increasing levels of sulfur in fossil fuel and the increasingly stringent regulation of sulfur emissions. Monticello et al., "Practical Considerations in Biodesulfurization of Petroleum," IGT's 3d Intl. Symp. on Gas, Oil, Coal and Env. Biotech., (Dec. 3–5, 1990) New Orleans, La.

Many biocatalysts and processes have been developed to desulfurize fossil fuels, including those described in U.S. Pat. Nos. 5,356,801, 5,358,870, 5,358,813, 5,198,341, 5,132,219, 5,344,778, 5,104,801 and 5,002,888, incorporated herein by reference. Economic analyses indicate that one limitation in the commercialization of the technology is improving the reaction rates and specific activities of the biocatalysts, such as the bacteria and enzymes that are involved in the desulfurization reactions. The reaction rates and specific activities (sulfur removed/hour/gram of biocatalyst) that have been reported in the literature are much lower than those necessary for optimal commercial technology. Therefore, improvements in the longevity and specific activity of the biocatalyst are desirable.

SUMMARY OF THE INVENTION

The invention relates to the discovery that a class of proteins, one of which was recently purified from *Rhodococcus sp.* IGTS8, activates two monooxygenases (DszC and DszA) involved in the desulfurization of fossil fuels. Neither DszC nor A are enzymatically active when purified to homogeneity; however, upon the addition of this additional protein (designated DszD herein), enzymatic activity is restored. The function of this protein is believed to couple the oxidation of NADH with the oxygenation of the substrate molecule. A search of the sequence databases revealed that DszD is equivalent to another recently identified Rhodococcus protein, ThcE, which is induced by growth in the presence of atrazine, thiocarbamate herbicides and primary alcohols. Based upon sequence similarity, ThcE appears to be a member of the group III alcohol dehydrogenases, or oxidoreductases, designated alcohol: N,N'-dimethyl-3-nitrosoaniline oxidoreductases. DszD has a monomer molecular weight of approximately 50,000 (by SDS-PAGE) but behaves as a multimeric protein (decamer) on HPLC size exclusion chromatography. The activation of DszC and A by DszD follows saturation kinetics.

Thus, the invention relates to the discovery that the rate of microbial desulfurization of fossil fuels is enhanced or activated by or dependent upon the addition of an oxidoreductase to the biocatalyst or reaction medium. The invention is drawn to a method for enhancing the rate of desulfurizing a fossil fuel containing organic sulfur compounds, comprising the steps of:

a) contacting the fossil fuel with an aqueous phase containing a biocatalyst or biocatalysts capable of cleaving carbon-sulfur bonds (such as Dsz A, Dsz B and/or Dsz C) and a rate-enhancing amount of an oxidoreductase, thereby forming a fossil fuel and aqueous phase mixture;

b) maintaining the mixture of step (a) under conditions sufficient for cleavage of the carbon-sulfur bonds of the organic sulfur molecules by the biocatalyst, thereby resulting in a fossil fuel having a reduced organic sulfur content; and c) separating the fossil fuel having a reduced organic sulfur content from the resulting aqueous phase.

The invention also relates to enhancing the rate of the reaction catalyzed by DszA and/or DszC with a rate enhancing amount of oxidoreductase. This can be accomplished, for example, by adding the oxidoreductase to a biocatalyst or by causing expression or overexpression of the oxidoreductase in a biocatalyst.

In yet another embodiment, the invention relates to a recombinant microorganism containing one or more recombinant DNA molecules which encode a biocatalyst capable of catalyzing one or more steps in a process for desulfurizing a fossil fuel containing organic sulfur molecules and which encode an oxidoreductase.

The invention includes a composition comprising (a) a biocatalyst capable of catalyzing one or more steps in a process for desulfurizing a fossil fuel containing organic sulfur molecules and (b) an oxidoreductase.

BRIEF DESCRIPTION OF THE DRAWINGS

FIG. 6 sets forth the DNA sequence and putative amino acid sequence of the ThcE (DszD) gene.

DETAILED DESCRIPTION OF THE INVENTION

Figure 1:
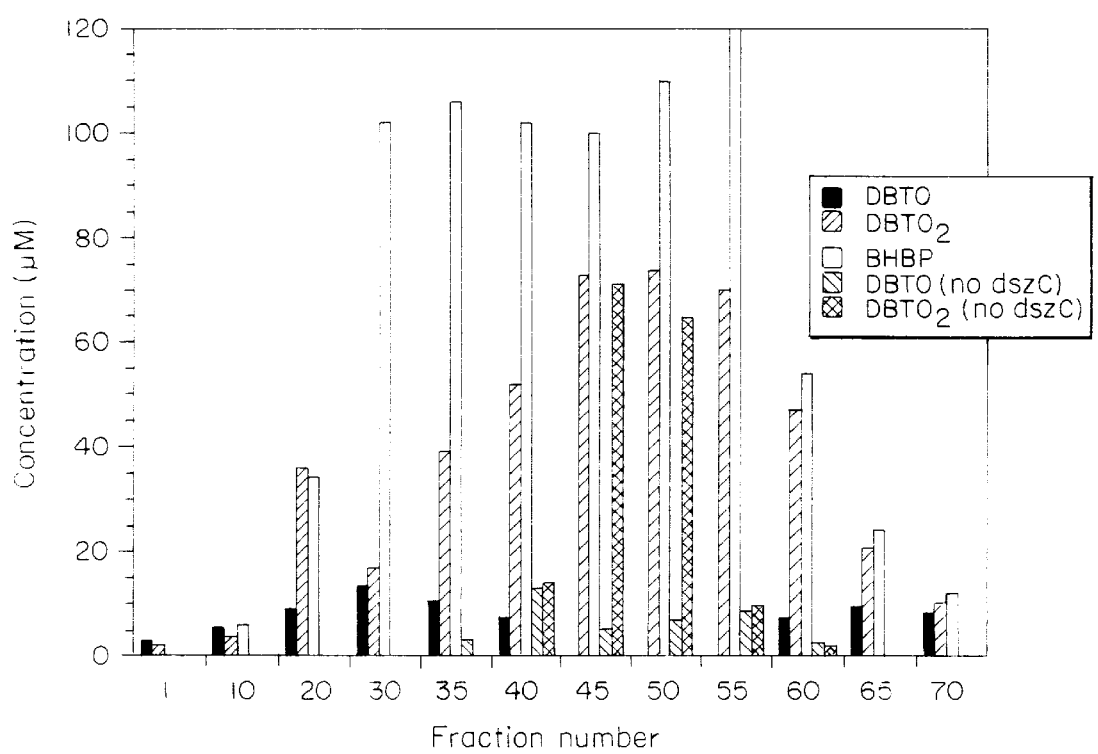
FIG. 1 is a graphic illustration of DszC and A activity after ion exchange chromatography. DszC (15 μg) was added to each fraction and tested for conversion from DBT to DBTO and DBTO2. DszA (5 μg) was added to each fraction and tested for DBT sultone to BHBP conversion. Endogenous DszC activity was also tested.

In the petroleum extraction and refining arts, the term "organic sulfur" is generally understood as referring to organic molecules having a hydrocarbon framework to which one or more sulfur atoms (called heteroatoms) are covalently joined. These sulfur atoms can be joined directly to the hydrocarbon framework, e.g., by one or more carbon-sulfur bonds, or can be present in a substituent joined to the hydrocarbon framework of the molecule, e.g., a sulfate group. The general class of organic molecules having one or more sulfur heteroatoms are referred to as "organosulfur compounds". The hydrocarbon portion of these compounds can be aliphatic, aromatic, or partially aliphatic and partially aromatic.

Cyclic or condensed multicyclic organosulfur compounds in which one or more sulfur heteroatoms are linked directly or indirectly to adjacent carbon atoms in the hydrocarbon framework by aromatic carbon-sulfur bonds are referred to as "sulfur-bearing heterocycles". The sulfur that is present in many types of sulfur-bearing heterocycles is referred to as "thiophenic sulfur" in view of the five-membered aromatic ring in which the sulfur heteroatom is present. The simplest such sulfur-bearing heterocycle is thiophene, which has the composition $C_4H_4S$.

Sulfur-bearing heterocycles are known to be stable to conventional desulfurization treatments, such as hydrodesulfurization (HDS). Sulfur-bearing heterocycles can have relatively simple or relatively complex chemical structures. In complex heterocycles, multiple condensed aromatic rings, one or more of which can be heterocyclic, are present. The difficulty of desulfurization increases with the structural complexity of the molecule. That is, refractory behavior is most accentuated in complex sulfur-bearing heterocycles, such as dibenzothiophene (DBT, $C_{12}H_8S$).

DBT is a sulfur-bearing heterocycle that has a condensed, multiple aromatic ring structure in which a five-membered thiophenic ring is flanked by two six-membered benzylic rings. Much of the residual post-HDS organic sulfur in fossil fuel refining intermediates and combustible products is thiophenic sulfur. The majority of this residual thiophenic sulfur is present as DBT and derivatives thereof having one or more alkyl or aryl groups attached to one or more carbon atoms present in one or both flanking benzylic rings. DBT itself is accepted in the relevant arts as a model compound illustrative of the behavior of the class of compounds encompassing DBT and derivatives thereof in reactions involving thiophenic sulfur. Monticello and Finnerty, *Annual Reviews in Microbiology* 39:371–389 (1985) at 372–373. DBT and derivatives thereof can account for a significant percentage of the total sulfur content of particular crude oils, coals and bitumen. For example, these sulfur-bearing heterocycles have been reported to account for as much as 70 wt % of the total sulfur content of West Texas crude oil, and up to 40 wt % of the total sulfur content of some Middle East crude oils. Thus, DBT is considered to be particularly relevant as a model compound for the forms of thiophenic sulfur found in fossil fuels, such as crude oils, coals or bitumen of particular geographic origin, and various refining intermediates and fuel products manufactured therefrom. Id. Another characteristic of DBT and derivatives thereof is that, following a release of fossil fuel into the environment, these sulfur-bearing heterocycles persist for long periods of time without significant biodegradation. Gundlach et al. *Science* 221:122–129 (1983). It is, therefore, desirable to remove these organosulfur compounds from fossil fuels or other carbonaceous materials which contain them.

A fossil fuel or carbonaceous material that is suitable for desulfurization treatment according to the present invention is one that contains organic sulfur. Such a fossil fuel is referred to as a "substrate fossil fuel". Substrate fossil fuels that are rich in thiophenic sulfur are particularly suitable for desulfurization according to the method described herein. Examples of such substrate fossil fuels include Cerro Negro or Orinoco heavy crude oils; Athabascan tar and other types of bitumen; petroleum refining fractions such as light cycle oil, heavy atmospheric gas oil, and No. 1 diesel oil; and coal-derived liquids manufactured from sources such as Pocahontas #3, Lewis-Stock, Australian Glencoe or Wyodak coal.

Biocatalytic desulfurization, or BDS, is the excision, liberation or removal of sulfur from organosulfur compounds, including refractory organosulfur compounds such as sulfur-bearing heterocycles, as a result of the oxidative cleavage (preferably selectively) of carbon-sulfur bonds in said compounds by a biocatalyst. BDS treatment yields the desulfurized hydrocarbon framework of the former refractory organosulfur compound, along with inorganic sulfur substances which can be readily separated from each other by known techniques such as fractional distillation or water extraction. For example, DBT is "converted" into hydroxybiphenyl when subjected to BDS treatment.

BDS is carried out by biocatalyst(s). Biocatalysts include one or more non-human organisms (e.g., recombinant and non-recombinant, viable and non-viable microorganisms) that functionally express one or more enzymes that direct, singly or in concert with each other, the removal of sulfur from organosulfur compounds, including sulfur-bearing heterocycles, by the oxidation of sulfur and/or the cleavage of carbon-sulfur bonds in said compounds; one or more enzymes obtained from such organisms; or a mixture of such organisms and enzymes. Organisms that exhibit one or more biocatalytic activities required for the desulfurization of a fossil fuel or other carbonaceous material are referred to herein as being Dsz+. Organisms that lack such a biocatalytic activity are referred to herein as being Dsz−. A "biocatalyst" is defined herein as a biological material, or a material of biological origin, which possesses the ability to catalyze one or more reactions, in the presence of appropriate co-factors and/or co-enzymes, for example.

The invention relates to the improved removal of sulfur from carbonaceous materials, such as fossil fuels, containing organic sulfur molecules comprising adding a rate-enhancing amount of an oxidoreductase to the biocatalyst capable of desulfurizing the carbonaceous material.

The biocatalysts employed herein are, generally, known in the art. Several investigators have reported the genetic modification of naturally-occurring bacteria into mutant strains capable of catabolizing DBT. Kilbane, J. J., *Resour. Cons. Recycl.* 3:69–79 (1990), Isbister, J. D., and R. C. Doyle, U.S. Pat. No. 4,562,156 (1985), and Hartdegan, F. J. et al., *Chem. Eng. Progress* 63–67 (1984). Many of these mutants desulfurize DBT nonspecifically. Thus, a portion of the fuel value is lost through this microbial action. Isbister and Doyle reported the derivation of a mutant strain of Pseudomonas which appeared to be capable of selectively liberating sulfur from DBT.

Kilbane has reported the mutagenesis of a mixed bacterial culture, thereby producing a bacterium which is capable of selectively liberating sulfur from DBT by an oxidative pathway. This culture was composed of bacteria which can be obtained from natural sources, such as sewage sludge, petroleum refinery wastewater, garden soil, coal, tar-contaminated soil, etc., and maintained in culture under conditions of continuous sulfur deprivation in the presence of DBT. The culture was then exposed to the chemical mutagen 1-methyl-3-nitro-1-nitrosoguanidine. The major catabolic product of DBT metabolism by this mutant culture was hydroxybiphenyl; sulfur was released as inorganic water-soluble sulfate, and the hydrocarbon portion of the molecule remained essentially intact as monohydroxybiphenyl. Kilbane, J. J., *Resour. Cons. Recycl.* 3:69–79 (1990), the teachings of which are incorporated herein by reference.

Kilbane has also isolated a mutant strain of Rhodococcus from this mixed bacterial culture. This mutant, IGTS8 or ATCC No. 53968, is a particularly preferred biocatalyst for use with the instant invention. The isolation and characteristics of this mutant are described in detail in J. J. Kilbane, U.S. Pat. No. 5,104,801, the teachings of which are incorporated herein by reference. This microorganism has been deposited at the American Type Culture Collection (ATCC), 12301 Park Lawn Drive, Rockville, Md., U.S.A. 20852 under the terms of the Budapest Treaty, and has been designated as ATCC Deposit No. 53968. One suitable ATCC No. 53968 biocatalyst preparation is a culture of the living microorganisms, prepared generally as described in U.S. Pat. No. 5,104,801 and mutants or derivatives thereof (see, e.g. U.S. Pat. No. 5,358,869). Cell-free enzyme preparations obtained from ATCC No. 53968 or mutants thereof generally as described in U.S. Pat. Nos. 5,132,219, 5,344,778 and 5,358,870 can also be used. These enzyme preparations can further be purified and employed.

Other examples of microorganisms that appear to behave in the same or similar manner include the microbial consortium (a mixture of several microorganisms) disclosed in Kilbane (1990), 3 Resour. Conserv. Recycl. 69–79, the microorganisms disclosed by Kilbane in U.S. Pat. Nos. 5,002,888 (issued Mar. 26, 1991), 5,104,801 (issued Apr. 14, 1992), 5,344,778, 5,132,219, 5,198,341, 5,344,778, 5,356,813, 5,356,801, 5,358,869, 5,358,870 [also described in Kilbane (1990), *Biodesulfurization: Future Prospects in Coal Cleaning,* in Proc, 7th Ann. Int'l. Pittsburgh Coal Conf. 373–382], and 5,198,341 (issued Mar. 30, 1993); and by Omori et al. (1992), *Desulfurization of dibenzothiophene by Corynebacterium sp. strain SY1,* 58 Appl. Env. Microbiol. (No. 3) 911–915; and Izumi et al., *Applied and Environmental Microbiology* 60:223–226 (1994) all incorporated herein by reference.

Each of the foregoing microorganisms can function as a biocatalyst in the present invention because each produces one or more enzymes (protein biocatalysts) that carry out the specific chemical reaction(s) by which sulfur is excised from refractory organosulfur compounds. Mutational or genetically engineered derivatives of any of the foregoing microorganisms, as exemplified by the U.S. patents listed above, can also be used as the biocatalyst herein, provided that appropriate biocatalytic function is retained.

Additional microorganisms suitable for use as the biocatalyst or biocatalyst source in the desulfurization process now described can be derived from naturally occurring microorganisms by known techniques. As set forth above, these methods include culturing preparations of microorganisms obtained from natural sources such as sewage sludge, petroleum refinery wastewater, garden soil, or coal, tar-contaminated soil under selective culture conditions in which the microorganisms are grown in the presence of refractory organosulfur compounds such as sulfur-bearing heterocycles as the sole sulfur source; exposing the microbial preparation to chemical or physical mutagens; or a combination of these methods. Such techniques are recounted by Isbister and Doyle in U.S. Pat. No. 4,562,156 (issued Dec. 31, 1985); by Kilbane in 3 Resour. Conserv. Recycl. 69–79 (1990), U.S. Pat. Nos. 5,002,888, 5,104,801 and 5,198,341; and by Omori and coworkers in 58 Appl. Env. Microbiol. (No. 3) 911–915 (1992), all incorporated by reference.

As explained above, enzymes are protein or peptide biocatalysts which can be made by living cells. Enzymes promote, direct or facilitate the occurrence of a specific chemical reaction or series of reactions (referred to as a pathway), generally, without themselves becoming consumed as a result thereof. Enzymes can include one or more unmodified or post-translationally or synthetically modified polypeptide chains or fragments or portions thereof, which catalyze the desired reaction or series of reactions when in the presence of the appropriate additional coenzymes, cofactors, or coreactants. The reaction or series of reactions relevant to one embodiment of the present invention culminates in the excision of sulfur from the hydrocarbon framework of a refractory organosulfur compound, such as a sulfur-bearing heterocycle. The hydrocarbon framework of the former refractory organosulfur compound remains substantially intact. Microorganisms or enzymes employed as biocatalysts in the present invention preferably and advantageously do not consume the hydrocarbon framework of the former refractory organosulfur compound as a carbon source for growth. As a result, the fuel value of substrate fossil fuels exposed to BDS treatment does not deteriorate.

Although living microorganisms (e.g., a culture) can be used as the biocatalyst herein, this is not required. Biocatalytic enzyme preparations that are useful in the present invention include microbial lysates, extracts, fractions, subfractions, or purified products obtained by conventional means and capable of carrying out the desired biocatalytic function. Generally, such enzyme preparations are substantially free of intact microbial cells. Kilbane and Monticello disclose enzyme preparations that are suitable for use herein in U.S. Pat. Nos. 5,132,219 (issued Jul. 21, 1992), and 5,358,870 (filed Jun. 11, 1992), for example. Rambosek et al. disclose recombinant microorganisms and enzyme preparations, engineered from *Rhodococcus sp.* ATCC No. 53968 and suitable for use herein, in U.S. Pat. No. 5,356,813. In a particularly preferred embodiment, the biocatalyst is overexpressed in the recombinant host cell (such as a cell which contains more than one copy of the gene or genes). For example, The desulfurization of dibenzothiophene by *Rhodococcus sp.* IGTS8 has been shown to involve at least three enzymes (designated DszA, B and C), of which DszA and C are now appreciated to be monooxygenases. As such, in a particularly preferred embodiment, the biocatalyst includes one or more of the enzymes, Dsz A, Dsz B and/or Dsz C.

Enzyme biocatalyst preparations suitable for use herein can optionally be affixed to a solid support, e.g., a membrane, filter, polymeric resin, glass particles or beads, or ceramic particles or beads. The use of immobilized enzyme preparations facilitates the separation of the biocatalyst from the reaction medium, such as the treated fossil fuel which has been depleted of refractory organosulfur compounds.

The specific activity of a given biocatalyst is a measure of its biocatalytic activity per unit mass. Thus, the specific activity of a particular biocatalyst depends on the nature or identity of the microorganism used or used as a source of biocatalytic enzymes, as well as the procedures used for preparing and/or storing the biocatalyst preparation. The concentration of a particular biocatalyst can be adjusted as desired for use in particular circumstances. For example, where a culture of living microorganisms (e.g., ATCC No. 53968) is used as the biocatalyst preparation, a suitable culture medium lacking a sulfur source other than sulfur-bearing heterocycles can be inoculated with suitable microorganisms and fermented until a desired culture density is reached. The resulting culture can be diluted with additional medium or another suitable buffer, or microbial cells present in the culture can be retrieved e.g., by centrifugation, and resuspended at a greater concentration than that of the original culture. The concentrations of microorganism and enzyme biocatalyst can be adjusted similarly. In this manner, appropriate volumes of biocatalyst preparations having predetermined specific activities and/or concentrations can be obtained.

As set forth above, a protein (designated DszD) has now been purified from *Rhodococcus sp.* IGTS8 which activates and enhances the activity of two monooxygenases integral in the biodesulfurization pathway (DszC and DszA). The function of this protein is believed to couple the oxidation of NADH with the oxygenation of the substrate molecules by DszA and DszC.. A search of the sequence databases revealed that DszD is equivalent to another recently isolated Rhodococcus protein, ThcE, which is reported to be induced by growth in the presence of atrazine, thiocarbamate herbicides and primary alcohols. ThcE is a member of the group III alcohol dehydrogenases, or oxidoreductases, designated alcohol: N,N'-dimethyl-3-nitrosoaniline oxidoreductases and has been described in Nagy et al., *Arch. Microbiol* (1995) 163: 439–446, which is incorporated herein by reference in its entirety. DszD has a monomer molecular weight of approximately 50,000 (by SDS-PAGE) but behaves as a multimeric protein (decamer) on HPLC size exclusion chromatography. The activation of DszC and A by DszD follows saturation kinetics.

In view of the above described discovery, desulfurization of DBT can be enhanced by the addition of an oxidoreductase. Suitable oxidoreductases include monooxygenase reductases, or alcohol oxidoreductases, such as N,N'-dimethyl-4-nitrosoaniline (NDMA)-dependent alcohol oxidoreductases (MNO). Group III alcohol dehydrogenases, or oxidoreductases, have been reported to oxidize a primary alcohol and reduce an electron acceptor, such as the nonphysiological compound NDMA. They generally contain a tightly but non-covalently bound molecule of $NAD^+$, which mediates electron transfer between an alcohol and the electron acceptor (e.g., NDMA). The term oxidoreductase is defined herein to include endogenous or wild-type enzymes, recombinantly produced enzymes, fusion proteins, active fragments, mutants or combinations thereof which possess the ability to enhance and/or activate the activity of DszA and/or DszC. Mutants include allelic variants, amino acid or site-directed mutations or derivatives (such as those prepared employing recombinant DNA technology). Alternatively mutants can be made employing other chemical or physical mutagenesis techniques with the host microorganism. The enzyme is preferably isolated from Rhodococcus or of rhodoccocal origin, such as IGTS8 or *Rhodococcus sp.* N186/21. Other preferred embodiments include recombinant oxidoreductases having an amino acid sequence highly homologous (such as, atleast about 90%) to the amino acid sequence of these enzymes. Alternatively homologous oxidoreductases, such as those which can be isolated from *Amycolatopsis methanolics* and *Mycobacterium gastri* can be employed.

As set forth above, oxidoreductases which can be employed herein include those generally known in the art and can be used directly as found in nature (e.g., a microbial fraction which contains the protein or enzyme), obtained commercially or can be made recombinantly. For example, the DNA and amino acid sequences of DszD is set forth in Nagy et al., *Arch Microbiology* (1995) 163:439–446 (and illustrated in FIG. 6) and can be used to transform a suitable host microorganism as is well known in the art and discussed in U.S. Pat. No. 5,356,801, for example. The DNA sequence can be isolated from a suitable Rhodococcus employing well known techniques, such as PCR.

In another embodiment, the oxidoreductase can be overexpressed by the desulfurization microorganism (such as IGTS8). This can be accomplished, for example, by mutagenesis. Suitable mutagens include radiation, e.g., ultraviolet radiation, and chemical mutagens, such as N-methyl-N'-nitrosoguanidine, hydroxylamine, ethylmethanesulfonate and nitrous acid. The mutagenesis and subsequent screening for mutants harboring increased enzymatic activity can be conducted according to methods generally known in the art.

Where the oxidoreductase is recombinant, the protein can be made and, preferably, overexpressed in situ, such as by the addition of a recombinant microorganism which contains one or more copies of a DNA sequence which encodes the oxidoreductase. In a particularly preferred embodiment, the recombinant microorganism encoding the oxidoreductase also possesses one or more enzymes capable of catalyzing one or more reactions in the biodesulfurization of a fossil fuel, particularly DszA and/or DszC. For example, the DNA encoding oxidoreductase, under control of a suitable promoter, can be transformed into IGTS8 or another microorganism capable of desulfurizing a fossil fuel. In another example, the DNA encoding the oxidoreductase is simultaneously (e.g., presented in a single plasmid or vector) or independently transformed into a common host cell with the DNA encoding the desulfurization biocatalyst(s) or enzymes. The DNA encoding the oxidoreductase can be, for example, under the control of the same or different promoter as the DNA encoding the biocatalyst capable of desulfurizing the fossil fuel. In one embodiment, the oxidoreductase DNA is incorporated or ligated into the desulfurization gene cluster or operon of IGTS8.

The oxidoreductase is added to the reaction mixture in a rate-enhancing amount. "Rate-enhancing amount," as defined herein, is an amount which will significantly increase the rate of reaction of the biocatalyst, as originally obtained, including activating the biocatalyst. For example, where the biocatalyst is IGTS8, a cell-free fraction or purified enzyme preparation thereof, a "rate-enhancing amount" of oxidoreductase is an amount of oxidoreductase that, in addition to that inherently present in the biocatalyst as obtained, will significantly increase the rate of desulfurization. The rate of desulfurization can be increased, for example, by at least 25%, 50% or 100% in comparison to the rate employing the biocatalyst per se. In one embodiment, the oxidoreductase is added to the reaction medium in an amount which achieves or approximates saturation kinetics.

The microorganism harboring the DNA sequence which encodes DszD can be grown under conditions which maximize the expression of the gene. Rhodococcus species which contain the gene can be grown in the presence of an alcohol (such as ethanol, ethanolamine, glycerol or propanol), aldehydes (such as, propionaldehyde), thiocarbamates or atrazine, for example. These compounds may induce or increase the expression of the gene in the microorganism.

As summarized above, the invention described herein relates in one aspect to a DNA molecule or fragment thereof containing a gene or genes which encode an oxidoreductase and/or a biocatalyst capable of desulfurizing a fossil fuel that contains organosulfur compounds. The DNA molecule or fragment thereof can be purified and isolated DNA obtained from, e.g., a natural source, or can be recombinant (heterologous or foreign) DNA that is, e.g., present in a non-human host organism. The DNA can be isolated by well knwon techniques, such as PCR, designing oligonucleotide primers from the nucleotide sequence set forth in FIG. 6.

The recombinant DNA molecules of the present invention include DNA resulting from the insertion into its chain, by chemical or biological means, of one or more genes encoding a biocatalyst capable of selectively cleaving carbon-sulfur bonds and an oxidoreductase, said gene not originally present in that chain. Recombinant DNA includes any DNA synthesized by procedures using restriction nucleases, nucleic acid hybridization, DNA cloning, DNA synthesis or any combination of the preceding. Methods of construction can be found in Maniatis et al., and in other methods known by those skilled in the art.

Procedures for the construction of the DNA plasmids or vectors of the present invention include those described in Maniatis et al. and other methods known by those skilled in the art. The terms "DNA plasmid" and "vector" are intended to encompass any replication competent plasmid or vector capable of having foreign or exogenous DNA inserted into it by chemical or biological means and subsequently, when transformed into an appropriate non-human host organism, of expressing the product of the foreign or exogenous DNA insert (e.g., of expressing the biocatalyst and oxidoreductase of the present invention). In addition, the plasmid or vector must be receptive to the insertion of a DNA molecule or fragment thereof containing the gene or genes of the present invention, said gene or genes encoding a biocatalyst, as defined above. Procedures for the construction of DNA plasmid vectors include those described in Maniatis et al. and others known by those skilled in the art.

The plasmids of the present invention include any DNA fragment containing a gene or genes encoding an oxidoreductase and/or a biocatalyst. The term "plasmid" is intended to encompass any DNA fragment. The DNA fragment should be transmittable, for example, to a host microorganism by transformation or conjugation. Procedures for the construction or extraction of DNA plasmids include those described in Maniatis et al. and others known by those skilled in the art.

The transformed non-human host organisms of the present invention can be created by various methods by those skilled in the art. For example, electroporation as explained by Maniatis et al. can be used. By the term "non-human host organism" is intended any non-human organism capable of the uptake and expression of foreign, exogenous or recombinant DNA. Preferably, the host organism is a bacterium, more preferably a pseudonomad.

In the biocatalytic desulfurization stage, the carbonaceous material or fossil fuel containing sulfur-bearing heterocycles is combined with the biocatalyst and oxidoreducase. The relative amounts of biocatalyst and oxidoreducase and carbonaceous material, such as a fossil fuel, can be adjusted to suit particular conditions, or to produce a particular level of residual sulfur in the treated, desulfurized material. The amount of biocatalyst preparation to be combined with a given quantity of substrate will reflect the nature, concentration and specific activity of the particular biocatalyst(s) and oxidoreductase used, as well as the nature and relative abundance of inorganic and organic sulfur compounds present in the substrate and the degree of desulfurization sought or considered acceptable.

The method of desulfurizing a fossil fuel of the present invention involves two aspects. First, a host organism or biocatalytic preparation obtained therefrom and oxidoreductase is contacted with a fossil fuel to be desulfurized. This can be done in any appropriate container, optionally fitted with an agitation or mixing device. The mixture is combined thoroughly and allowed to incubate for a sufficient time to allow for cleavage of a significant number of carbon-sulfur bonds in organosulfur compounds, thereby producing a desulfurized fossil fuel. In one embodiment, an aqueous emulsion or microemulsion is produced with an aqueous culture of the organism or enzyme fraction and the fossil fuel, allowing the organism to propagate in the emulsion while the expressed biocatalyst cleaves carbon-sulfur bonds.

Variables such as temperature, mixing rate and rate of desulfurization will vary according to the organism biocatalyst and/or oxidoreductase, used. The parameters can be determined through no more than routine experimentation.

Several suitable techniques for monitoring the rate and extent of desulfurization are well-known and readily available to those skilled in the art. Baseline and time course samples can be collected from the incubation mixture, and prepared for a determination of the residual organic sulfur in the fossil fuel. The disappearance of sulfur from organosulfur compounds, such as DBT, in the sample being subjected to biocatalytic treatment can be monitored using, e.g., X-ray fluorescence (XRF) or atomic emission spectrometry (flame spectrometry). Preferably, the molecular components of the sample are first separated, e.g., by gas chromatography.

The process and the biocatalytic compositions (including the recombinant microorganisms) of the claimed invention result in a significant and unexpected improvement over earlier disclosed processes of desulfurization. It has been shown that in vitro the reactions catalyzed by purified DszA and DszC proteins are activated by the addition of the oxidoreductase. This is particularly unexpected in view of recent discussions in the literature suggesting that FAD binds directly to DszC (Denome et al., J. Bacteriol., 176:6707–6716, 1994) and the suggestion that NADH is the only cofactor required for the system (Ohshiro et al., FEMS Microbiol. Lett. 118:341–344, 1994). Others suggest that DszABC are the sole enzymes responsible for desulfurization to occur (Piddington, et al., Appl. Env. Microbiol., 67:468–475, 1995).

Without being limited to any particular mechanism or theory, it is believed that the pathway of the desulfurization reaction is set forth below:

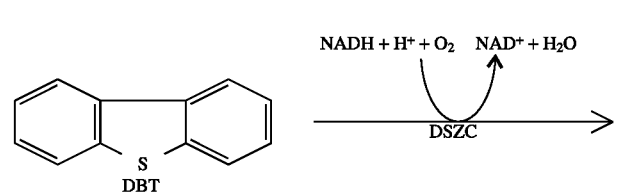

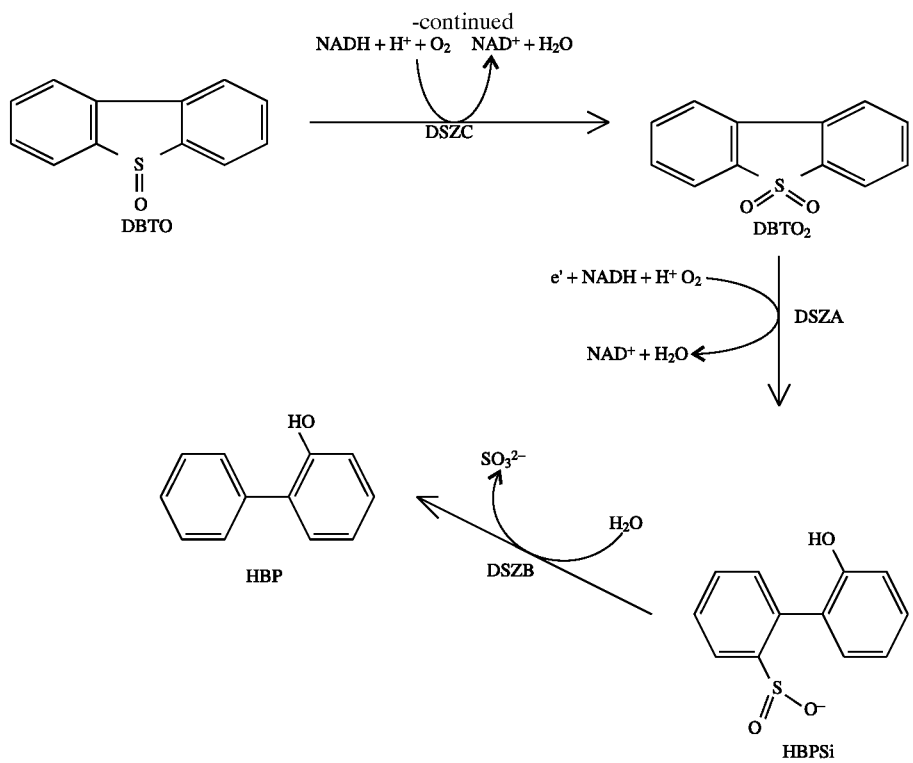

Here, the oxidoreductase is believed to be a short electron transport chain to deliver the reducing equivalents from NADH (or other electron donor) to the enzymes, DszC and/or DszA (possibly a physiological electron acceptor of the oxidoreductase). The enzyme DszC is believed to be responsible for the biocatalysis of the oxidation reaction of DBT to DBTO2. The enzyme DszA is believed to be responsible for the oxygenation of DBTO2 to phenolphenylsulfite (PPS).

It is particularly preferred to add the cofactor, FMN, to the reaction medium as well as an electron donor, NADH or NADPH. Also preferred is the addition of an NADH or NADPH regeneration system for converting NAD+ to NADH, according to methods known in the art.

The invention will now be further illustrated by the way of the following examples.

EXEMPLIFICATION
Growth of *Rhodococcus sp.* IGTS8

A sample of frozen stock of *Rhodococcus sp.* IGTS8 strain CPE-648 containing plasmid pENOK3 (genotype of DszA-B-C+) as described by Piddington et al. (*Appl. Environ. Microbiol.* 61:468–475 (1995)) was grown in 500 ml of rich medium in a 2000 ml shake flask for 48 hours at 30° C. This culture was used to inoculate (4% inoculum) a 15 Liter NBS fermentater in the same medium. This culture was grown for 48 hours at 30° C. while controlling pH (between 6.8 and 7.3), agitation and dissolved oxygen (>50% saturated). Finally a 5% inoculum was transferred to a production-scale fermentater (300 Liter Chemap) containing basal salts medium, 0.5 g/L Ivanhoe antifoam, 8 g/l ethanol and 1.5 mM dimethyl sulfoxide. The culture was grown for 45 hours, achieving an optical density of 11, with a doubling time of 4.3 hours during the first 24 hours of the run. The cell suspension was concentrated through a Westfalia centrifuge resulting in the production of about 2.5 kg. of wet cell paste. The paste was stored at −70° C. until used for purification.

Purification of DszD 150 g (wet cell paste) of the Rhodococcus as grown above were resuspended in 25 mM NaPi, pH 7.5 (buffer A) containing 100 mM NaCl, 0.5 mM DTT, 1' mM PMSF and DNAse. The cell suspension was passed two times through a French pressure cell (at 20,000 psi) and then centrifuged at 30,000×g for 45 minutes (5° C.) to remove unbroken cells and cell debris. All subsequent chromatography steps were performed at 4° C. using a Pharmacia FPLC system. The supernatant was loaded into a Q-sepharose column (2.6 cm×20 cm) equilibrated with buffer A containing 100 mM NaCl. Following loading the column was washed extensively with the same buffer until the OD280 of the eluent was close to zero. The column was developed with a linear gradient from 100 mM NaCl to 500 mM NaCl in buffer A for 180 minutes at a flow rate of 5 mL/minute and 10 mL fractions were collected. The fractions which displayed DszD activity were pooled and dialyzed overnight vs. buffer A. The dialysate was loaded onto a Toyopearl DEAE-650M column (2.6 cm×10 cm) equilibrated with buffer A. The column was developed with a linear gradient from 0 to 200 mM NaCl for 90 minutes at a flow rate of 4 mL/minute and 4 mL fractions were collected. The fractions which contained DszD activity were pooled and dialyzed overnight vs. buffer A. The dialysate was loaded onto a Pharmacia MonoQ column equilibrated with buffer A. The column was developed with a linear gradient from 160 to 300 mM NaCl for 30 minutes at a flow rate of 0.5 mL/minute and 0.5 mL fractions were collected. The fractions which displayed DszD activity were pooled and concentrated to 0.2 mL using Amicon microconcentrators (molecular weight cutoff of 10 kDa). The concentrated sample was then applied to a Pharmacia Superdex 75 size exclusion column equilibrated with buffer A containing 100 mM NaCl. The column was eluted with the same buffer at a flow rate of 0.2 mL/minute and 0.2 mL fractions were collected. The fractions containing DszD activity were pooled and concentrated using the microconcentrators and the protein was stored on ice until used. SDS-PAGE analysis (14% polyacrylamide) of the final preparation showed a single band with an approximate monomer molecular weight of 50,000 Da.

Enzyme Assays

DszD activity was measured by monitoring DBTO and DBTO2 production from DBT as catalyzed by the combination of DszC and DszD. The DszC was obtained from an *E. coli* expression system, previously described. The assay (in 25 mM NaPi pH 7.5, 100 mM NaCl and 0.5 mM DTT) contained DszC (between 6 and 15 μg), 3 mM NADH, 10 μM FMN, 100 μM DBT and the sample containing DszD. The assay mixture was allowed to incubate at 30° C. with shaking at 300 rpm for some period of time (typically 15 to 60 minutes). The reaction was stopped by the addition of acetonitrile (to 50%) and the products analyzed by reversed phase HPLC. Activation of DszA by DszD was assayed in the same manner (DszA was also obtained from an *E. coli* expression system) except that the substrate was DBT sultone and the product was 2,2'-dihydroxybiphenyl (BHBP).

Results

Purification of DszD

Figure 2:
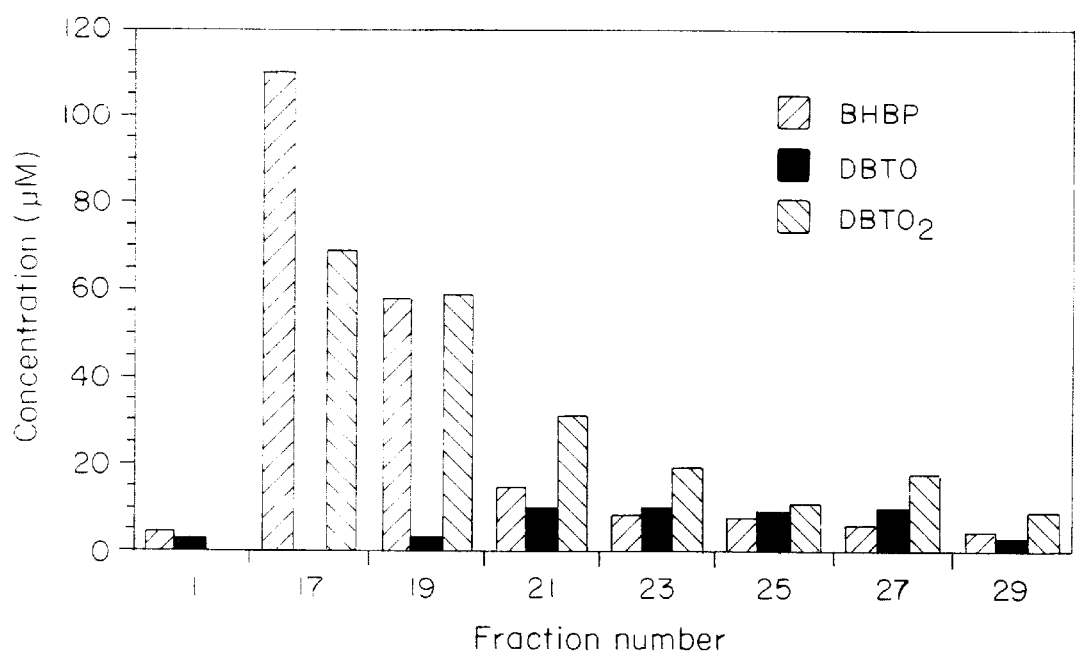
FIG. 2 is a graphic illustration of DszC activity after Superdex 75 size exclusion chromatography. DszC (15 μg) was added to each fraction and tested for conversion from DBT to DBTO2. DszA activity after Superdex 75 size exclusion chromatography. DszA (5 μg) was added to each fraction and tested for DBTsultone to BHBP conversion.
Figure 3:
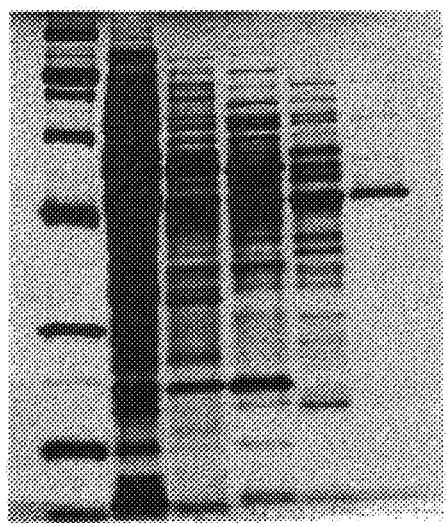
FIG. 3 is an electrophoretic gel illustrating SDS-PAGE (14% acrylamide) of the purification of DszD. Lane 1 presents the molecular weight standards (Biorad, 200, 116, 97.4, 66, 45, 31, 21.5 and 14.5 kDa); lane 2, crude cell lysate; lane 3, after Q-sepharose; lane 4, after Toyopearl-DEAE; lane 5, after MonoQ, and; lane 6, after Superdex 75.

FIG. 1 shows the DszD activity profile of the fractions from the first anion exchange column (Q-sepharose). As can be seen by these data the activity starts around fraction 20 and extends to about fraction 60. Both DszA and C activation occurs in these reactions, furthermore the endogenous DszC activity is also present in these fractions (notably fractions 40 to 50). Fractions 40 to 60 were pooled and further separated on Toyopearl—DEAE. An activity pattern similar to the Q-sepharose column was observed after the Toyopearl—DEAE chromatography except that the activity eluted at a lower salt concentration and endogenous DszC activity occurred in later fractions (a small amount of activity in fraction 40). This was further substantiated by Western analysis which showed that DszC eluted with a peak between fraction 45 and 50 (data not shown). Fractions 15 to 35 were pooled and applied to the MonoQ column. The active fractions from this column were pooled, concentrated and further separated by chromatography over a Superdex 75 FPLC column. The activity profile of this column is shown in FIG. 2. This figure shows that both DszA and C are activated by protein(s) in the same fractions. SDS-PAGE analysis (FIG. 3) showed that the final preparation consisted of a single polypeptide of molecular weight approximately 50,000. HPLC analysis using a TosoHaas TSK3000SW size exclusion column on a Hewlett Packard 1050 HPLC system showed a single protein peak eluted at an approximate mass of 500,000 Da indicating that the native protein is most likely a decamer.

DszD activation of DszC and DszA

Figure 4:
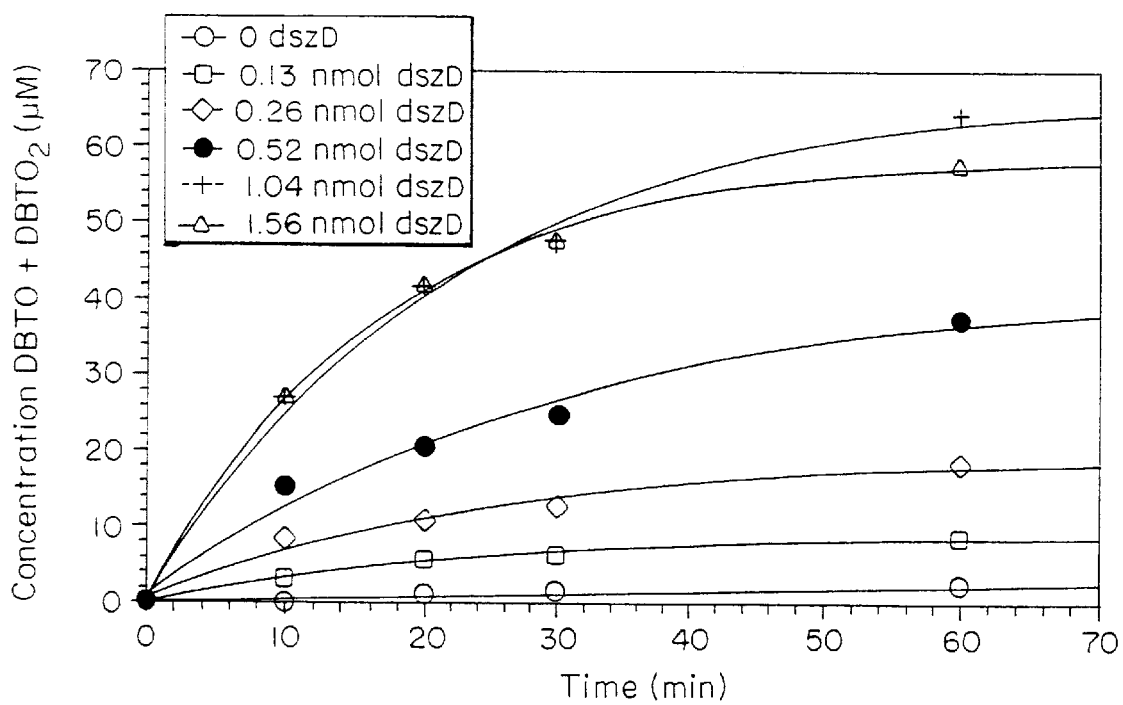
FIG. 4 illustrates the activation of DszC by the addition of increasing amounts of DszD. A fixed amount of DszC (0.33 nmol)) was titrated with increasing amounts of DszD.
Figure 5:
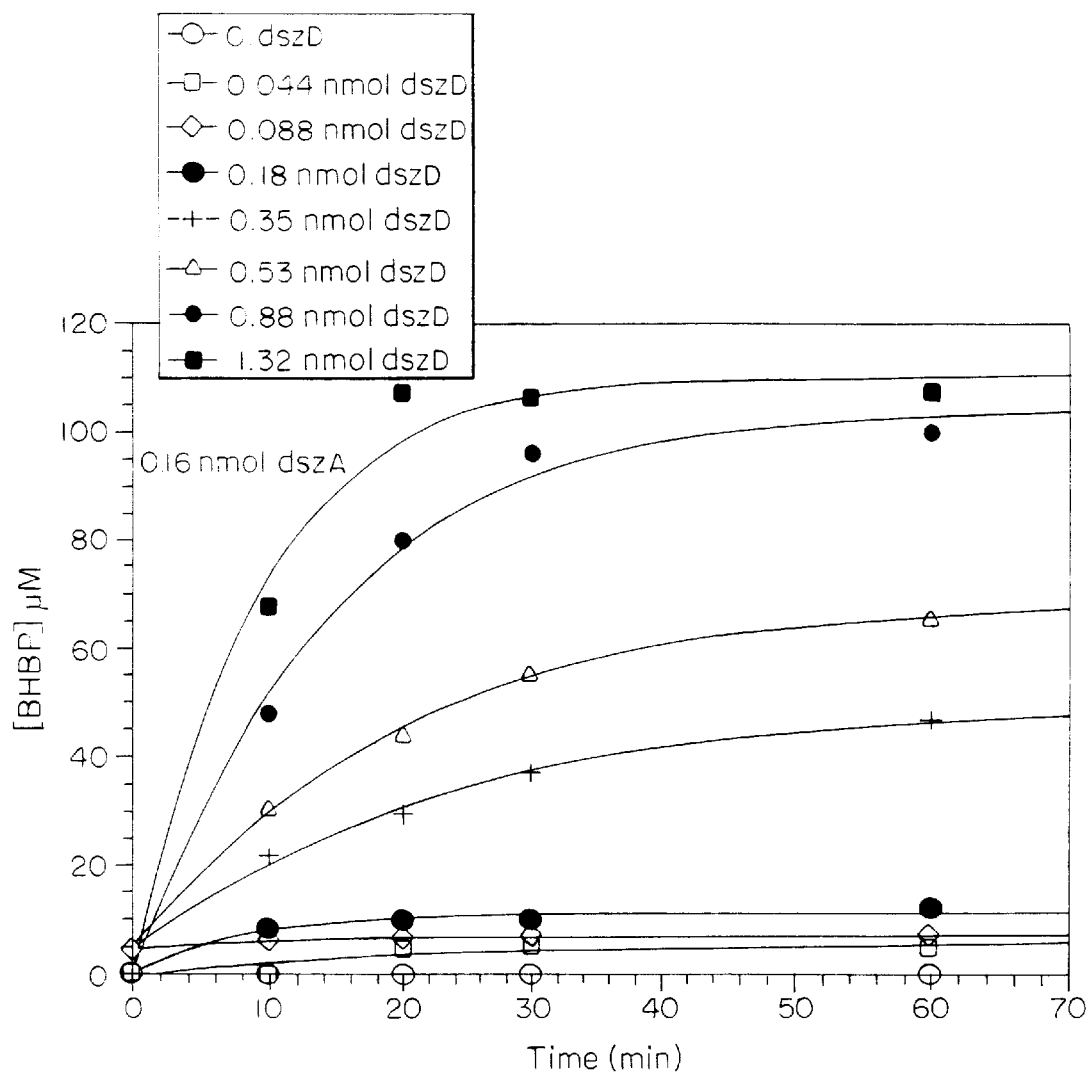
FIG. 5 illustrates activation of DszA by increasing amounts of DszD. A fixed amount of DszA (0.16 nmol) was titrated with increasing amounts of DszD.

FIG. 4 shows that the activation of DszC by DszD follows saturation kinetics. As the ratio between DszD and C is increased an increased rate of DBTO2 formation is observed. A plot of the initial rate vs. DszD:DszC shows that saturation is achieved. FIG. 5 shows the result of activation of DszA by the same preparation. The same effect is observed, i.e. as more DszD is added an increase in the DszA reaction rate occurs.

Amino Acid Sequence of DszD

DszD was subjected to N-terminal sequence and the following sequence was obtained (one letter amino acid abbreviations):

H2N-AIELNQIWDFPIKEFHPFPRALMGVGAHD IIGVE-AKNLGFKRTLLM-COOH (SEQ ID. NO: 3)

A search of the data-bases resulted in a 100% match with a Rhodococcus protein designated ThcE (Nagy et al., *Arch. Microbiol.* 163:439–446 (1995)). The DNA sequence and putative amino acid sequences of the open reading frames are set forth in FIG. 6. This protein has high homology to the alcohol: N,N'-dimethyl-4-nitrosoaniline (NDMA) oxidoreductses found in other Gram-positive organisms which are involved in the oxidation of alcohols and the concomitant reduction of an electron acceptor. The physiological electron acceptor in those organisms is unknown.

EQUIVALENTS

Those skilled in the art will know, or be able to ascertain, using no more than routine experimentation, many equivalents to the specific embodiments of the invention described herein. These and all other equivalents are intended to be encompassed by the following claims.

We claim:

1. A method for enhancing the rate of biodesulfurization of a fossil fuel containing organic sulfur compounds, comprising the steps of:
    a) contacting the fossil fuel with an aqueous phase containing a biocatalyst which oxidatively cleaves carbon-sulfur bonds in a nicotinamide adenial dinucleotide dependent manner and an additional rate-enhancing amount of a group III alcohol dehydrogenase, thereby forming a fossil fuel and aqueous phase mixture;
    b) maintaining the mixture of step a) under conditions sufficient for cleavage of the carbon-sulfur bonds of the organic sulfur molecules by the biocatalyst, thereby resulting in a fossil fuel having a reduced organic sulfur content; and
    c) separating the fossil fuel having a reduced organic sulfur content from the resulting aqueous phase.

2. The method of claim 1 wherein the group III alcohol dehydrogenase is N,N'-dimethyl-4-nitrosoaniline-dependent alcohol oxidoreductase.

3. The method of claim 1 wherein the group III alcohol dehydrogenase is of Rhodococcus origin.

4. The method of claim 3 further comprising adding NADH or NADPH and flavin.

5. The method of claim 4 wherein the fossil fuel is a liquid hydrocarbon.

6. The method of claim 4 wherein the biocatalyst which cleaves carbon-sulfur bonds is a microorganism.

7. The method of claim 6 wherein the microorganism contains a recombinant DNA molecule which encodes one or more enzymes which cleave carbon-sulfur bonds.

8. The method of claim 7 wherein the recombinant DNA molecule is derived from *Rhodococcus sp.* ATCC 53968.

9. The method of claim 4 wherein the biocatalyst which cleaves carbon-sulfur bonds is a cell-free fraction.

10. The method of claim 9 wherein the biocatalyst is a cell-free fraction of *Rhodococcus sp.* ATCC 53968.

11. The method of claim 4 wherein the biocatalyst comprises one or more enzymes or enzyme fractions derived from a microorganism which cleaves carbon-sulfur bonds.

12. The method of claim 11 wherein the microorganism is *Rhodococcus sp.* ATCC 53968.

13. The method of claim 4 wherein the biocatalyst which cleaves carbon sulfur bonds and group III alcohol dehydrogenase are recombinantly produced by a single microorganism.

14. A method for enhancing the rate of reaction of a carbonaceous material containing organic sulfur compounds, comprising the steps of:

a) contacting the material with an aqueous phase containing a biocatalyst which oxidizes carbon-sulfur bonds in a nicotinamide adenine dinucleotide-dependent manner and an additional rate-enhancing amount of a group III alcohol dehydrogenase; and b) maintaining the mixture of step a) under conditions sufficient for reaction of the organic sulfur compounds by the biocatalyst.

15. The method of claim 14 wherein the group III alcohol dehydrogenase is N,N'-dimethyl-4-nitrosoaniline-dependent alcohol oxidoreductase.

16. The method of claim 14 wherein the group III alcohol dehydrogenase is of Rhodococcus origin.

17. The method of claim 16 wherein the biocatalyst is a monooxygenase.

18. The method of claim 16 wherein the biocatalyst is a DszA or DszC.

19. The method of claim 18 further comprising adding NADH or NADPH and flavin.

20. The method of claim 19 wherein the sulfur containing compound is a substituted or unsubstituted dibenzothiophene.

* * * * *

UNITED STATES PATENT AND TRADEMARK OFFICE
CERTIFICATE OF CORRECTION

PATENT NO. : 5,846,813
DATED : December 8, 1998
INVENTOR(S) : Kevin A. Gray, Charles H. Squires and Daniel J. Monticello It is certified that error appears in the above-identified patent and that said Letters Patent is hereby corrected as shown below:

Column 22, line 66 in Claim 6 delete "4" and insert --3-- therefor.

Column 23, line 6 in Claim 9 delete "4" and insert --3-- therefor.

Column 23, line 10 in Claim 11 delete "4" and insert --3-- therefor.

Column 23, line 15 in Claim 13 delete "4" and insert --3-- therefor.

Signed and Sealed this

Twentieth Day of April, 1999

*Attest:*

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2063 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 382..1652

( i x ) FEATURE:
        ( A ) NAME/KEY: CDS
        ( B ) LOCATION: 1743..2062

( x i ) SEQUENCE DESCRIPTION: SEQ ID NO:1:

```
GGTACCTCGA CTGTCGTCAT CGCGAAGCTA GTCCTCTCGT GAAGCTGGGT AAAGCGCAGG        60

TCAGTGAAGT GCAACATCTA GAACGTGTTC TAGTTCAATG TTAGCAGTGA TGAAAAGCTA       120

CTGGGGATCG TAGTCGCCGA GCAACACGTT CCCGATCAGC GGGAACCACG GCAGTCTGAT       180

CCGGCCTTCC TGGCGGTCCG GGTGGCGAC  GACCTGCCCG AACGGGCGGT TCGCCGGCGG       240

CGTCCGGGCG GTTGAGCTGC CGAAGTCTGT GCACGGGGTG TTTGTCGGTA CACAGTGGGA       300

ACCAGGTGAG ACGCCGGTCA CAAAGAATCG GCTCGAATCC CTCCCGCAGT CATATTCGTG       360

CACATCCATG AGGAGATACC G ATG GCT ATC GAG CTC AAC CAG ATC TGG GAC         411
                       Met Ala Ile Glu Leu Asn Gln Ile Trp Asp
                        1           5                       10
```

```
TTT CCG ATC AAG GAG TTC CAC CCC TTC CCG CGC GCC CTG ATG GGT GTG         459
Phe Pro Ile Lys Glu Phe His Pro Phe Pro Arg Ala Leu Met Gly Val
                15                  20                      25

GGC GCT CAC GAC ATC ATC GGT GTG GAG GCC AAG AAT CTC GGC TTC AAG         507
Gly Ala His Asp Ile Ile Gly Val Glu Ala Lys Asn Leu Gly Phe Lys
            30                  35                      40

CGC ACC CTT CTG ATG ACG ACC GGT CTG CGC GGT TCG GGC ATC ATC GAG         555
Arg Thr Leu Leu Met Thr Thr Gly Leu Arg Gly Ser Gly Ile Ile Glu
            45                  50                      55

GAA CTC GTC GGC AAG ATC GAG TAC CAG GGT GTC GAG GTC GTG CTC TAC         603
Glu Leu Val Gly Lys Ile Glu Tyr Gln Gly Val Glu Val Val Leu Tyr
        60              65                  70

GAC AAG GTC GAG TCG AAT CCC AAG GAC TAC AAC GTC ATG GAG GCC GCG         651
Asp Lys Val Glu Ser Asn Pro Lys Asp Tyr Asn Val Met Glu Ala Ala
 75              80                  85                      90

GCT CTC TAT CAG AAG GAG AAG TGC GAC TCG ATC ATC TCG ATC GGC GGT         699
Ala Leu Tyr Gln Lys Glu Lys Cys Asp Ser Ile Ile Ser Ile Gly Gly
                95                  100                     105

GGT TCG AGC CAC GAC GCC GCC AAG GGT GCT CGC GTC GTG ATC GCA CAC         747
Gly Ser Ser His Asp Ala Ala Lys Gly Ala Arg Val Val Ile Ala His
            110                 115                     120

GAC GGT CGC AAC ATC AAC GAG TTC GAG GGC TTC GCC AAG TCC ACC AAC         795
Asp Gly Arg Asn Ile Asn Glu Phe Glu Gly Phe Ala Lys Ser Thr Asn
            125                 130                     135

AAG GAG AAC CCG CCG CAT ATC GCC GTA TCC ACT ACG GCT GGA ACG GGT         843
Lys Glu Asn Pro Pro His Ile Ala Val Ser Thr Thr Ala Gly Thr Gly
    140                 145                 150

TCC GAG ACG TCG TGG GCA TAC GTC ATC ACT GAC ACC TCG GAC ATG AAC         891
Ser Glu Thr Ser Trp Ala Tyr Val Ile Thr Asp Thr Ser Asp Met Asn
155                 160                 165                 170

AAC CCG CAC AAG TGG GTG GGC TTC GAC GAG GCG ACC ATC GTC ACG TTG         939
Asn Pro His Lys Trp Val Gly Phe Asp Glu Ala Thr Ile Val Thr Leu
                175                 180                 185

GCG ATC GAC GAT CCG CTG CTC TAC TAC ACC TGC CCT CAG CAT TTC ACC         987
Ala Ile Asp Asp Pro Leu Leu Tyr Tyr Thr Cys Pro Gln His Phe Thr
            190                 195                 200

GCG TAC TGC GGC TTC GAC GTA CTC GCG CAC GGC AGT GAG CCT TTC GTT        1035
Ala Tyr Cys Gly Phe Asp Val Leu Ala His Gly Ser Glu Pro Phe Val
        205                 210                 215

TCT CGT CTC GAT TTC GCG CCT TCG CTC GGT AAC GCG ATC TAC TCG GTC        1083
Ser Arg Leu Asp Phe Ala Pro Ser Leu Gly Asn Ala Ile Tyr Ser Val
    220                 225                 230

GAG TTG GTC GCG AAG AAC CTG CGC GAG GCC GTC TTC GAG CCG CGT AAC        1131
Glu Leu Val Ala Lys Asn Leu Arg Glu Ala Val Phe Glu Pro Arg Asn
235                 240                 245                 250

CTC AAG GCG CGC GAG GGA ATG ATG AAC GCG CAG TAC ATT GCC GGA CAG        1179
Leu Lys Ala Arg Glu Gly Met Met Asn Ala Gln Tyr Ile Ala Gly Gln
                255                 260                 265
```

```
GCC  TTC  AAC  TCC  GGT  GGC  CTC  GGC  ATC  GTT  CAC  TCG  ATC  TCG  CAC  GCG   1227
Ala  Phe  Asn  Ser  Gly  Gly  Leu  Gly  Ile  Val  His  Ser  Ile  Ser  His  Ala
               270                 275                      280

GTC  AGT  GCA  TTC  TTC  GAC  AGC  CAC  CAC  GGT  TTG  AAC  AAC  GCC  ATC  GCG   1275
Val  Ser  Ala  Phe  Phe  Asp  Ser  His  His  Gly  Leu  Asn  Asn  Ala  Ile  Ala
          285                      290                           295

TTG  CCG  CGT  GTG  TGG  GAG  TAC  AAC  CTG  CCT  TCG  CGT  TAC  GAG  CGC  TAC   1323
Leu  Pro  Arg  Val  Trp  Glu  Tyr  Asn  Leu  Pro  Ser  Arg  Tyr  Glu  Arg  Tyr
     300                      305                      310

GCC  CAG  TTG  GCC  GGC  GCA  CTC  GGT  GTC  GAC  ACT  CGC  AAC  CTC  ACC  ACG   1371
Ala  Gln  Leu  Ala  Gly  Ala  Leu  Gly  Val  Asp  Thr  Arg  Asn  Leu  Thr  Thr
315                      320                      325                      330

GTT  CAG  GCC  GCG  GAT  GCT  GCC  GTC  GAG  GCT  GCC  ATT  CGT  CTG  GCC  AAG   1419
Val  Gln  Ala  Ala  Asp  Ala  Ala  Val  Glu  Ala  Ala  Ile  Arg  Leu  Ala  Lys
                    335                      340                      345

GAC  GTC  GGT  ATC  CCC  GAC  AAC  TTC  GGG  CAG  GTT  CGC  ACA  GAC  TCG  TAC   1467
Asp  Val  Gly  Ile  Pro  Asp  Asn  Phe  Gly  Gln  Val  Arg  Thr  Asp  Ser  Tyr
               350                      355                      360

GCG  AAG  AAC  CAG  ATG  AAC  ACC  AAG  AAG  TAC  GAG  GGT  CGT  GGT  GAT  GTC   1515
Ala  Lys  Asn  Gln  Met  Asn  Thr  Lys  Lys  Tyr  Glu  Gly  Arg  Gly  Asp  Val
          365                      370                      375

ATC  AAG  GGT  GAC  GAG  AAG  ACT  GTG  CGC  GCC  ATC  TCC  GAG  CAC  ATT  CAG   1563
Ile  Lys  Gly  Asp  Glu  Lys  Thr  Val  Arg  Ala  Ile  Ser  Glu  His  Ile  Gln
     380                      385                      390

GAC  GAC  TGG  TGC  ACC  CCG  GGT  AAC  CCC  CGT  GAG  GTC  ACT  GTG  GAG  TCG   1611
Asp  Asp  Trp  Cys  Thr  Pro  Gly  Asn  Pro  Arg  Glu  Val  Thr  Val  Glu  Ser
395                      400                      405                      410

ATG  ATC  CCG  GTT  GTC  GAT  CAC  GCG  ATC  AAC  AAG  TCG  TAC  TT              1652
Met  Ile  Pro  Val  Val  Asp  His  Ala  Ile  Asn  Lys  Ser  Tyr
                    415                      420

CTAGCAGGGC  CTCCGGCCCC  GTGCGCGCTT  AAGGAGTCCA  GAGACTCCTC  GAGCGCGCAC           1712

AGGGGCTGTG  CCCCTATCGA  AAGGTATTCC  ATG  TCC  GGT  CGC  AGT  TTC  TCC  AGC       1766
                                    Met  Ser  Gly  Arg  Ser  Phe  Ser  Ser
                                     1                    5

GGA  ATC  GAA  GTG  AAA  GAT  GCT  CTG  CGA  GAG  CAG  GAC  TAC  ATT  GCC  GAT   1814
Gly  Ile  Glu  Val  Lys  Asp  Ala  Leu  Arg  Glu  Gln  Asp  Tyr  Ile  Ala  Asp
          10                       15                        20

GAC  GAG  TTC  GCG  GTA  GTC  GTT  CAT  CTG  GCG  ACG  GCG  CTG  GGG  CGT  CCG   1862
Asp  Glu  Phe  Ala  Val  Val  Val  His  Leu  Ala  Thr  Ala  Leu  Gly  Arg  Pro
25                       30                       35                       40

CTC  CTG  CTC  GAA  GGG  CCG  GCC  GGT  GTC  GGT  AAG  ACG  GAA  CTG  GCG  AAG   1910
Leu  Leu  Leu  Glu  Gly  Pro  Ala  Gly  Val  Gly  Lys  Thr  Glu  Leu  Ala  Lys
                    45                       50                            55

TCT  CTG  GCT  GCG  ATC  GGG  GGC  CGC  AAA  CTG  GTG  CGA  TTG  CAG  TGT  TAC   1958
Ser  Leu  Ala  Ala  Ile  Gly  Gly  Arg  Lys  Leu  Val  Arg  Leu  Gln  Cys  Tyr
               60                       65                            70

GAA  GGG  CTG  GAC  GAC  AAT  CGA  GCC  CTG  TAC  GAA  TGG  GAC  TAC  GCG  AAC   2006
Glu  Gly  Leu  Asp  Asp  Asn  Arg  Ala  Leu  Tyr  Glu  Trp  Asp  Tyr  Ala  Asn
          75                       80                        85

GAA  CTC  CTG  CAC  GTG  CAG  ATG  CTT  CGC  GAC  CGG  ATC  AGT  GAT  CAG  GTT   2054
Glu  Leu  Leu  His  Val  Gln  Met  Leu  Arg  Asp  Arg  Ile  Ser  Asp  Gln  Val
     90                       95                       100

TCC  GAA  TT  C                                                                  2063
Ser  Glu
105
```

(2) INFORMATION FOR SEQ ID NO:2:

(i) SEQUENCE CHARACTERISTICS:
        (A) LENGTH: 423 amino acids
        (B) TYPE: amino acid ( D ) TOPOLOGY: linear ( i i ) MOLECULE TYPE: protein ( x i ) SEQUENCE DESCRIPTION: SEQ ID NO:2:

| Met | Ala | Ile | Glu | Leu | Asn | Gln | Ile | Trp | Asp | Phe | Pro | Ile | Lys | Glu | Phe |
|---|---|---|---|---|---|---|---|---|---|---|---|---|---|---|---|
| 1 | | | | 5 | | | | | 10 | | | | | 15 | |

| His | Pro | Phe | Pro | Arg | Ala | Leu | Met | Gly | Val | Gly | Ala | His | Asp | Ile | Ile |
|---|---|---|---|---|---|---|---|---|---|---|---|---|---|---|---|
| | | | 20 | | | | | 25 | | | | | 30 | | |

| Gly | Val | Glu | Ala | Lys | Asn | Leu | Gly | Phe | Lys | Arg | Thr | Leu | Leu | Met | Thr |
|---|---|---|---|---|---|---|---|---|---|---|---|---|---|---|---|
| | | | 35 | | | | | 40 | | | | | 45 | | |

| Thr | Gly | Leu | Arg | Gly | Ser | Gly | Ile | Ile | Glu | Glu | Leu | Val | Gly | Lys | Ile |
|---|---|---|---|---|---|---|---|---|---|---|---|---|---|---|---|
| | 50 | | | | | 55 | | | | | | 60 | | | |

| Glu | Tyr | Gln | Gly | Val | Glu | Val | Val | Leu | Tyr | Asp | Lys | Val | Glu | Ser | Asn |
|---|---|---|---|---|---|---|---|---|---|---|---|---|---|---|---|
| 65 | | | | | 70 | | | | | 75 | | | | | 80 |

| Pro | Lys | Asp | Tyr | Asn | Val | Met | Glu | Ala | Ala | Leu | Tyr | Gln | Lys | Glu |
|---|---|---|---|---|---|---|---|---|---|---|---|---|---|---|
| | | | | 85 | | | | 90 | | | | | 95 | |

| Lys | Cys | Asp | Ser | Ile | Ile | Ser | Ile | Gly | Gly | Ser | Ser | His | Asp | Ala |
|---|---|---|---|---|---|---|---|---|---|---|---|---|---|---|
| | | | | 100 | | | | 105 | | | | 110 | | |

| Ala | Lys | Gly | Ala | Arg | Val | Val | Ile | Ala | His | Asp | Gly | Arg | Asn | Ile | Asn |
|---|---|---|---|---|---|---|---|---|---|---|---|---|---|---|---|
| | | 115 | | | | | 120 | | | | | 125 | | | |

| Glu | Phe | Glu | Gly | Phe | Ala | Lys | Ser | Thr | Asn | Lys | Glu | Asn | Pro | Pro | His |
|---|---|---|---|---|---|---|---|---|---|---|---|---|---|---|---|
| | 130 | | | | | 135 | | | | | 140 | | | | |

| Ile | Ala | Val | Ser | Thr | Thr | Ala | Gly | Thr | Gly | Ser | Glu | Thr | Ser | Trp | Ala |
|---|---|---|---|---|---|---|---|---|---|---|---|---|---|---|---|
| 145 | | | | | 150 | | | | | 155 | | | | | 160 |

| Tyr | Val | Ile | Thr | Asp | Thr | Ser | Asp | Met | Asn | Asn | Pro | His | Lys | Trp | Val |
|---|---|---|---|---|---|---|---|---|---|---|---|---|---|---|---|
| | | | | 165 | | | | | 170 | | | | | 175 | |

| Gly | Phe | Asp | Glu | Ala | Thr | Ile | Val | Thr | Leu | Ala | Ile | Asp | Asp | Pro | Leu |
|---|---|---|---|---|---|---|---|---|---|---|---|---|---|---|---|
| | | | 180 | | | | | 185 | | | | | 190 | | |

| Leu | Tyr | Tyr | Thr | Cys | Pro | Gln | His | Phe | Thr | Ala | Tyr | Cys | Gly | Phe | Asp |
|---|---|---|---|---|---|---|---|---|---|---|---|---|---|---|---|
| | | 195 | | | | | 200 | | | | | 205 | | | |

| Val | Leu | Ala | His | Gly | Ser | Glu | Pro | Phe | Val | Ser | Arg | Leu | Asp | Phe | Ala |
|---|---|---|---|---|---|---|---|---|---|---|---|---|---|---|---|
| | 210 | | | | | 215 | | | | | 220 | | | | |

| Pro | Ser | Leu | Gly | Asn | Ala | Ile | Tyr | Ser | Val | Glu | Leu | Val | Ala | Lys | Asn |
|---|---|---|---|---|---|---|---|---|---|---|---|---|---|---|---|
| 225 | | | | | 230 | | | | | 235 | | | | | 240 |

| Leu | Arg | Glu | Ala | Val | Phe | Glu | Pro | Arg | Asn | Leu | Lys | Ala | Arg | Glu | Gly |
|---|---|---|---|---|---|---|---|---|---|---|---|---|---|---|---|
| | | | | 245 | | | | | 250 | | | | | 255 | |

| Met | Met | Asn | Ala | Gln | Tyr | Ile | Ala | Gly | Gln | Ala | Phe | Asn | Ser | Gly | Gly |
|---|---|---|---|---|---|---|---|---|---|---|---|---|---|---|---|
| | | | 260 | | | | | 265 | | | | | 270 | | |

| Leu | Gly | Ile | Val | His | Ser | Ile | Ser | His | Ala | Val | Ser | Ala | Phe | Phe | Asp |
|---|---|---|---|---|---|---|---|---|---|---|---|---|---|---|---|
| | | 275 | | | | | 280 | | | | | 285 | | | |

| Ser | His | His | Gly | Leu | Asn | Asn | Ala | Ile | Ala | Leu | Pro | Arg | Val | Trp | Glu |
|---|---|---|---|---|---|---|---|---|---|---|---|---|---|---|---|
| | 290 | | | | | 295 | | | | | 300 | | | | |

| Tyr | Asn | Leu | Pro | Ser | Arg | Tyr | Glu | Arg | Tyr | Ala | Gln | Leu | Ala | Gly | Ala |
|---|---|---|---|---|---|---|---|---|---|---|---|---|---|---|---|
| 305 | | | | | 310 | | | | | 315 | | | | | 320 |

| Leu | Gly | Val | Asp | Thr | Arg | Asn | Leu | Thr | Thr | Val | Gln | Ala | Ala | Asp | Ala |
|---|---|---|---|---|---|---|---|---|---|---|---|---|---|---|---|
| | | | | 325 | | | | | 330 | | | | | 335 | |

| Ala | Val | Glu | Ala | Ala | Ile | Arg | Leu | Ala | Lys | Asp | Val | Gly | Ile | Pro | Asp |
|---|---|---|---|---|---|---|---|---|---|---|---|---|---|---|---|
| | | | 340 | | | | | 345 | | | | | 350 | | |

| Asn | Phe | Gly | Gln | Val | Arg | Thr | Asp | Ser | Tyr | Ala | Lys | Asn | Gln | Met | Asn |
|---|---|---|---|---|---|---|---|---|---|---|---|---|---|---|---|
| | | 355 | | | | | 360 | | | | | 365 | | | |

| Thr | Lys | Lys | Tyr | Glu | Gly | Arg | Gly | Asp | Val | Ile | Lys | Gly | Asp | Glu | Lys |
|---|---|---|---|---|---|---|---|---|---|---|---|---|---|---|---|
| | 370 | | | | | 375 | | | | | 380 | | | | |

| Thr | Val | Arg | Ala | Ile | Ser | Glu | His | Ile | Gln | Asp | Asp | Trp | Cys | Thr | Pro |
|---|---|---|---|---|---|---|---|---|---|---|---|---|---|---|---|
| 385 | | | | | 390 | | | | | 395 | | | | | 400 |

```
Gly  Asn  Pro  Arg  Glu  Val  Thr  Val  Glu  Ser  Met  Ile  Pro  Val  Val  Asp
               405                411                          415

His  Ala  Ile  Asn  Lys  Ser  Tyr
               420
```

(2) INFORMATION FOR SEQ ID NO:3:

(i) SEQUENCE CHARACTERISTICS:
        (A) LENGTH: 106 amino acids
        (B) TYPE: amino acid
        (D) TOPOLOGY: linear (ii) MOLECULE TYPE: protein (xi) SEQUENCE DESCRIPTION: SEQ ID NO:3:

```
Met  Ser  Gly  Arg  Ser  Phe  Ser  Ser  Gly  Ile  Glu  Val  Lys  Asp  Ala  Leu
 1                    5                         10                        15

Arg  Glu  Gln  Asp  Tyr  Ile  Ala  Asp  Asp  Glu  Phe  Ala  Val  Val  Val  His
               20                        25                    30

Leu  Ala  Thr  Ala  Leu  Gly  Arg  Pro  Leu  Leu  Leu  Glu  Gly  Pro  Ala  Gly
          35                         40                         45

Val  Gly  Lys  Thr  Glu  Leu  Ala  Lys  Ser  Leu  Ala  Ala  Ile  Gly  Gly  Arg
     50                         55                         60

Lys  Leu  Val  Arg  Leu  Gln  Cys  Tyr  Glu  Gly  Leu  Asp  Asp  Asn  Arg  Ala
65                       70                         75                       80

Leu  Tyr  Glu  Trp  Asp  Tyr  Ala  Asn  Glu  Leu  Leu  His  Val  Gln  Met  Leu
               85                         90                        95

Arg  Asp  Arg  Ile  Ser  Asp  Gln  Val  Ser  Glu
                    100                 105
```

(2) INFORMATION FOR SEQ ID NO:4:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
Ala  Ile  Glu  Leu  Asn  Gln  Ile  Trp  Asp  Phe  Pro  Ile  Lys  Glu  Phe  His
 1                    5                         10                        15

Pro  Phe  Pro  Arg  Ala  Leu  Met  Gly  Val  Gly  Ala  His  Asp  Ile  Ile  Gly
               20                        25                    30

Val  Glu  Ala  Lys  Asn  Leu  Gly  Phe  Lys  Arg  Thr  Leu  Leu  Met
          35                         40                    45
```